(12) United States Patent
Pan-Montojo et al.

(10) Patent No.: US 10,182,999 B2
(45) Date of Patent: Jan. 22, 2019

(54) GLYCOLIC ACID ENHANCES SPERM MOBILITY

(71) Applicant: MAX-PLANCK-GESELLSCHAFT ZUR FORDERUNG DER WISSENSCHAFTEN E.V., Munich (DE)

(72) Inventors: Francisco Pan-Montojo, Munich (DE); Teymuras Kurzchalia, Berlin (DE); Anthony A. Hyman, Dresden (DE)

(73) Assignee: Francisco Pan-Montojo, Munich (DE)

( * ) Notice: Subject to any disclaimer, the term of this patent is extended or adjusted under 35 U.S.C. 154(b) by 0 days.

(21) Appl. No.: 15/505,132

(22) PCT Filed: Aug. 18, 2015

(86) PCT No.: PCT/EP2015/068917
§ 371 (c)(1),
(2) Date: Feb. 20, 2017

(87) PCT Pub. No.: WO2016/026843
PCT Pub. Date: Feb. 25, 2016

(65) Prior Publication Data
US 2017/0239201 A1  Aug. 24, 2017

(30) Foreign Application Priority Data
Aug. 18, 2014 (EP) ..................... 14181284

(51) Int. Cl.
*A61K 31/19* (2006.01)
*A61K 45/06* (2006.01)
(Continued)

(52) U.S. Cl.
CPC ............ *A61K 31/19* (2013.01); *A61K 9/0034* (2013.01); *A61K 9/0036* (2013.01); *A61K 9/06* (2013.01); *A61K 45/06* (2013.01)

(58) Field of Classification Search
None
See application file for complete search history.

(56) References Cited

U.S. PATENT DOCUMENTS

| | | |
|---|---|---|
| 5,153,230 A | 10/1992 | Jaffery |
| 2004/0171144 A1 | 9/2004 | Brackett |

(Continued)

FOREIGN PATENT DOCUMENTS

CN        103352025 B      4/2015

OTHER PUBLICATIONS

Dr. Alex Polyakov, "Male Infertility", pp. 1-6, [retrieved from on-line website: http://www.dralexpolyakov.com.au/services/male-infertility/, last access date: Apr. 10, 2018]. (Year: 2018).*

(Continued)

*Primary Examiner* — Ernst V Arnold
*Assistant Examiner* — Kyung S Chang
(74) *Attorney, Agent, or Firm* — Avery N. Goldstein; Blue Filament Law PLLC

(57) ABSTRACT

The present invention relates to glycolic acid or a pharmaceutically acceptable salt or ester thereof for use in the treatment or prevention of male infertility. The present invention also relates to an ex vivo method for increasing the mobility of spermatozoa comprising contacting glycolic acid or a pharmaceutically acceptable salt or ester thereof with spermatozoa.

12 Claims, 7 Drawing Sheets

Figure 1:
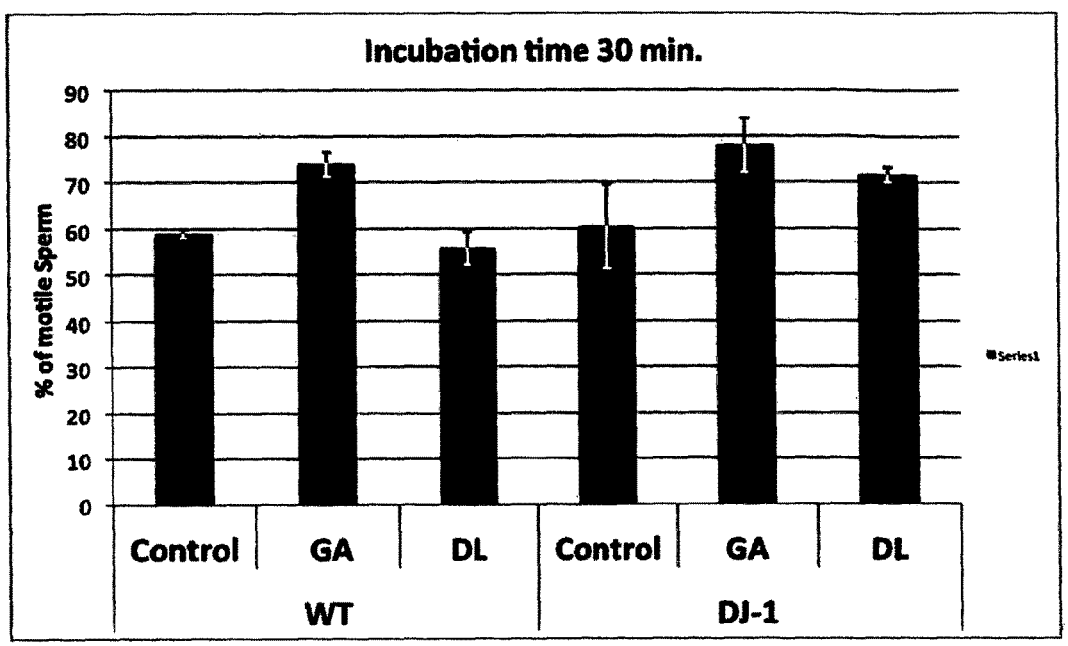

(51) Int. Cl.
*A61K 9/06* (2006.01)
*A61K 9/00* (2006.01)

(56) References Cited

U.S. PATENT DOCUMENTS

2005/0100519 A1  5/2005  Guth et al.
2007/0060620 A1  3/2007  Sefton
2010/0062039 A1  3/2010  Shalaby

OTHER PUBLICATIONS

Male Infertility, Mayo Clinic, 2018, pp. 1-11 (Year: 2018).*
Curi et al., "Asthenozoospermia: Analysis of a large population", Journal of Reproductive Systems, published online: Jul. 9, 2009, pp. 343-349. (Year: 2009).*
Srivastava, S. and Agarwal, A., "Effect of anion channel blockers on L-arginine action in spermatozoa from asthenospermic men", Andrologia, Mar. 17, 2010, pp. 76-82, vol. 42, issue 2, Copyright Blackwell Verlag GmbH (2010).
Harris, K.S. and Richardson, K.E., "Glycolate in the diet and its conversion to urinary oxalate in the rat", Investigative Urology, Sep. 1980, pp. 106-109, vol. 18, issue 2, Copyright © 1980 by the Williams & Wilkins Co.
Maheshwari, Abha, Hamilton, Mark, and Bhattacharya, Siladitya, "Effect of female age on the diagnostic categories of infertility", Human Reproduction, Jan. 11, 2008, pp. 538-542, vol. 23, issue 3, Oxford University Press on behalf of the European Society of Human Reproduction and Embryology (2008).
Broekhuijse, M.L.W.J., Feitsma, H., and Gadella, B.M., "Artificial insemination in pigs: predicting male fertility", Veterinary Quarterly, Dec. 2012, pp. 151-157, vol. 32, issues 3-4, Taylor & Francis (2012).
Franken, Daniel R. And Oehninger, Sergio, "Semen analysis and sperm function testing", Asian Journal of Andrology, Dec. 19, 2011, pp. 6-13, vol. 14, issue 1, U.S.A.
Ortega, C. et al., "Absolute asthenozoospermia and ICSI: what are the options?", Human Reproduction Update, Aug. 3, 2011, pp. 684-692, vol. 17, issue 5, Oxford University Press on behalf of the European Society of Human Reproduction and Embryology (2011).
Eunice Kennedy Shriver National Institute of Child Health and Human Development, "Infertility and Fertility", 2017, 2 pages, https://www.nichd.nih.gov/health/topics/infertility/Pages/default.aspx.
Gerris, J., "Methods of semen collection not based on masturbation of surgical sperm retrieval", Human Reproduction Update, Mar. 10, 1999, pp. 211-215, vol. 5, issue 3, European Society of Human Reproduction and Embryology (1999).
Lafuente, Rafael et al., "Coenzyme Q10 and male infertility: a meta-analysis", Journal of Assisted Reproduction and Genetics, Aug. 3, 2013, pp. 1147-1156, vol. 30, Springer Science+Business Media New York (2013), U.S.A.
Mancini, Antonio and Balercia, Giancarlo, "Coenzyme Q10 in male infertility: Physiopathology and therapy", Biofactors, Sep./Oct. 2011, pp. 374-380, vol. 37, issue 5, International Union of Biochemistry and Molecular Biology, Inc. (2011).
Walczak-Jedrzejowska, Renata, Wolski, Jan Karol, and Slowikowska-Hilczer, Jolanta, "The role of oxidative stress and antioxidants in male fertility", Central European Journal of Urology, 2013, pp. 60-67, vol. 66, issue 1, Warsaw, Poland.
Anagnostis, Panagiotis, Karras, Spiros, and Goulis, Dimitrios G., "Vitamin D in human reproduction: A narrative review", International Journal of Clinical Practice, Mar. 2013, pp. 225-235, vol. 67, issue 3, Blackwell Publishing Ltd (2013).
Manee-In, S. et al., "L-carnitine Supplemented Extender Improves Cryopreserved-thawed Cat Epididymal Sperm Motility", Asian-Australasian Journal of Animal Sciences, Jun. 2014, pp. 791-796, vol. 27, issue 6, Asian-Australasian Journal of Animal Sciences (2014).
Schurmann, A. et al., "Reduced Sperm Count and Normal Fertility in Male Mice with Targeted Disruption of the ADP-Ribosylation Factor-Like 4 (Arl4) Gene", Molecular and Cellular Biology, Apr. 2002, pp. 2761-2768, vol. 22, issue 8, American Society for Microbiology (2002).
International Search Report dated Nov. 9, 2015 for International Application No. PCT/EP2015/068917 filed Aug. 18, 2015.
Riffo, M. et al., "Effect of zinc on human sperm motility and the acrosome reaction", International Journal of Andrology, 1992, pp. 229-237, vol. 15, issue 3; DOI: 10.1111/j.1365-2605.1992.tb01343.x.
Makar, Robert S. et al., "The Evaluation of Infertility", American Journal of Clinical Pathology, Jun. 2002, pp. S95-S103, vol. 117 (Suppl. 1), © American Society for Clinical Pathology.
Zhou, Ji et al., "The Semen pH Affects Sperm Motility and Capacitation", PLoS ONE, Jul. 14, 2015, 15 pages, vol. 10, issue 7: e0132974, © 2015 Zhou et al.; DOI:10.1371/journal.pone.0132974.

* cited by examiner

A

Figure 8:
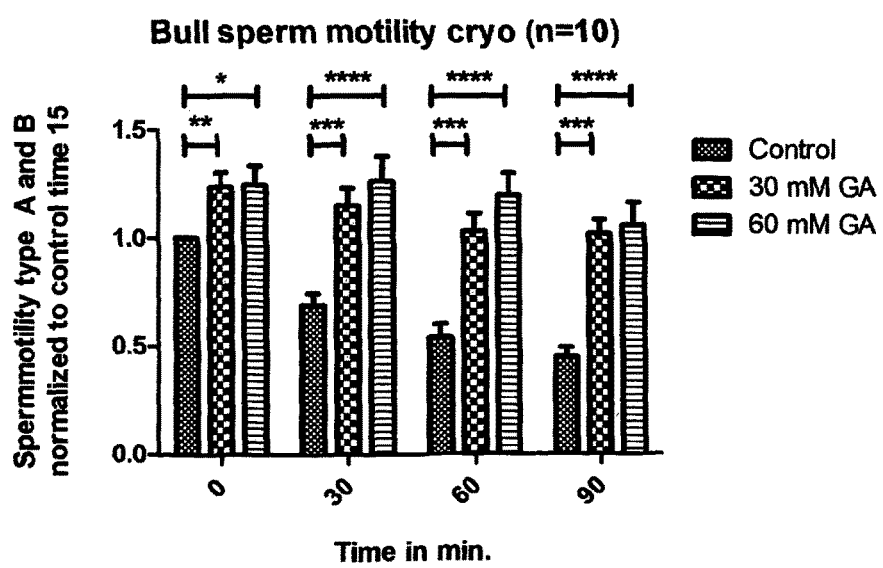

Figure 8 – continued
B
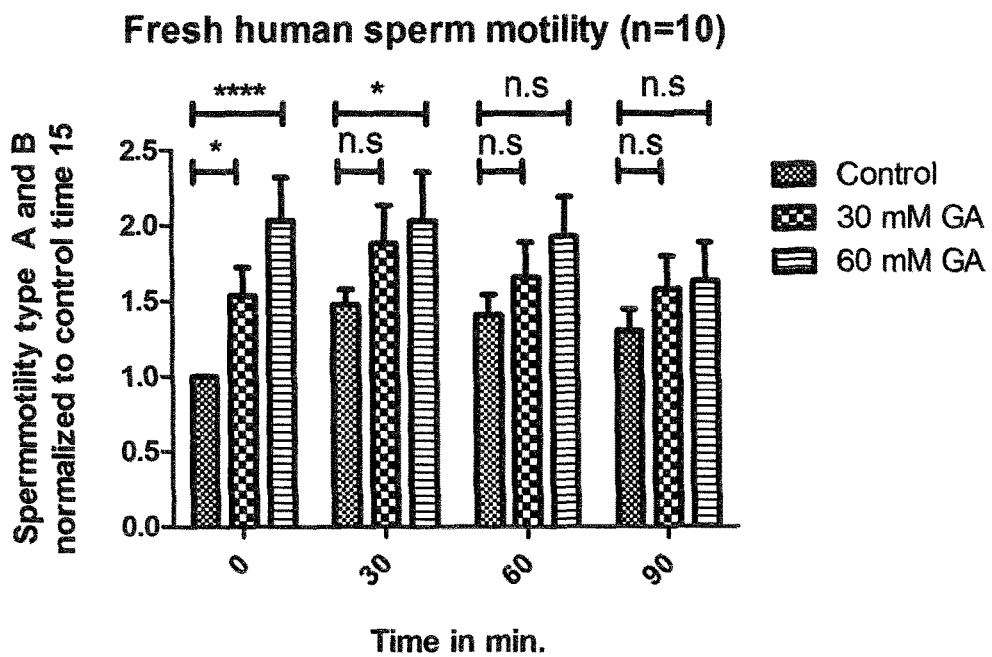
C
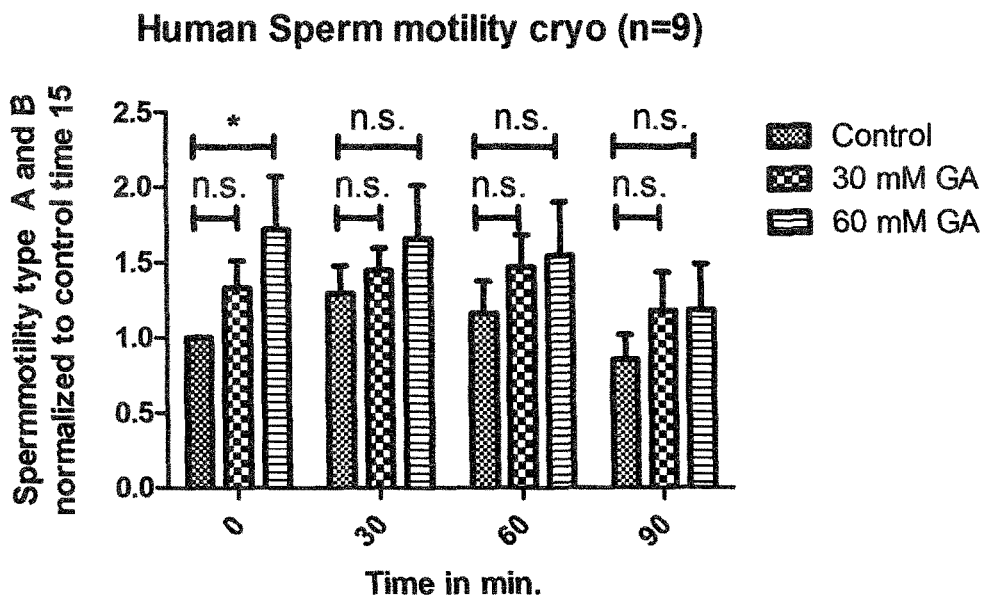

Figure 8 – continued
D
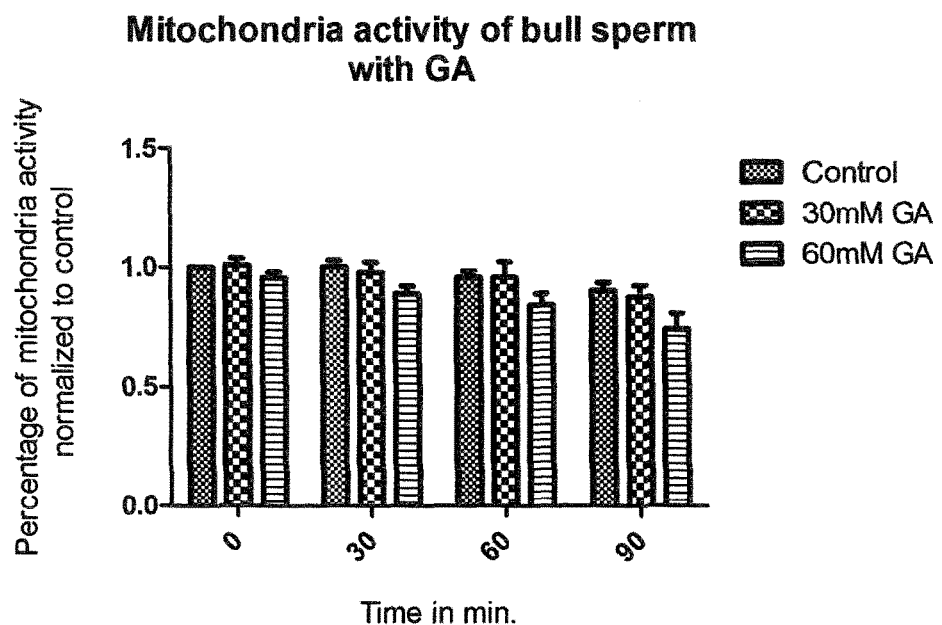
E
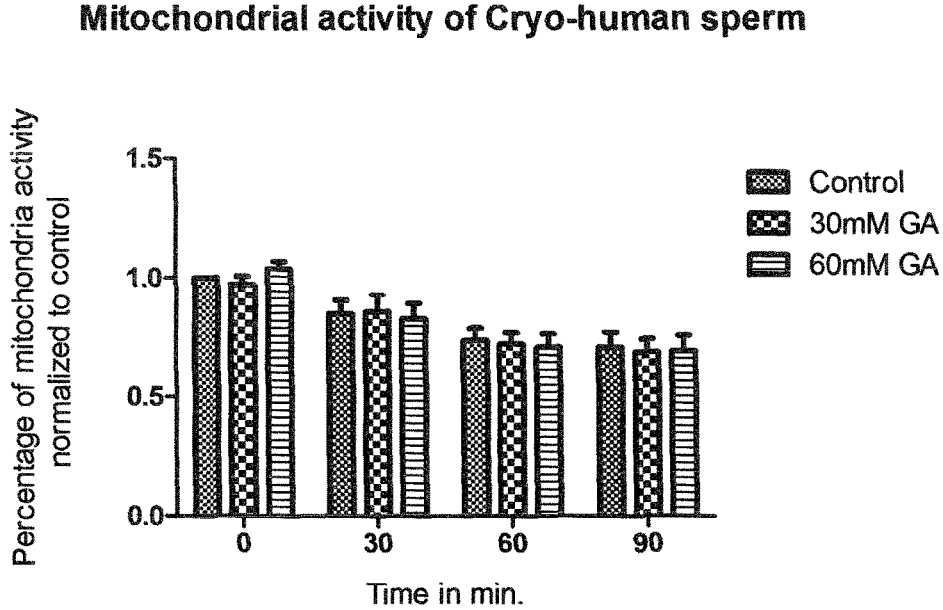

Figure 8 – continued
F
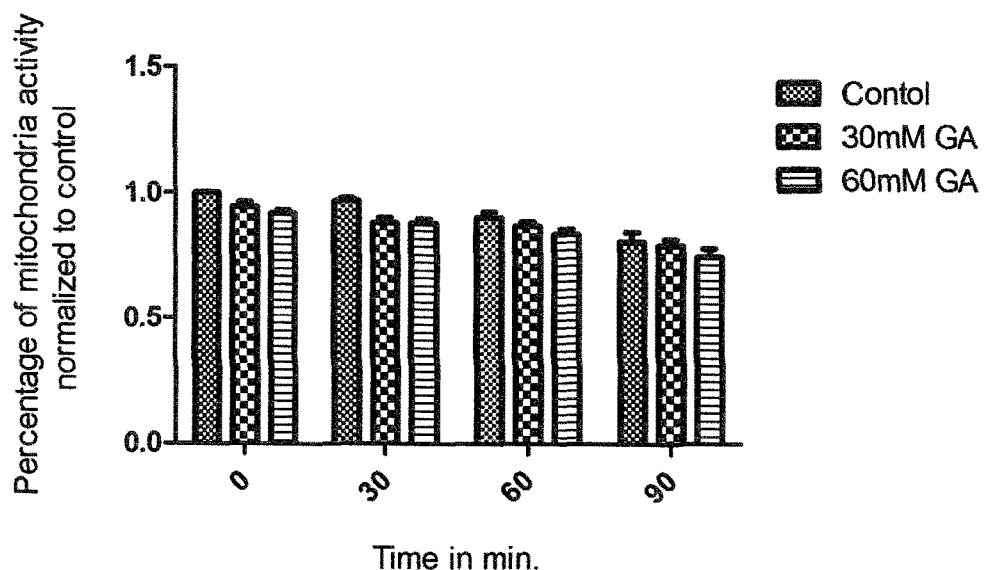

GLYCOLIC ACID ENHANCES SPERM MOBILITY

The present invention relates to glycolic acid or a pharmaceutically acceptable salt or ester thereof for use in the treatment or prevention of male infertility. The present invention also relates to an ex vivo method for increasing the mobility of spermatozoa comprising contacting glycolic acid or a pharmaceutically acceptable salt or ester thereof with spermatozoa.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Infertility is fundamentally the inability to conceive offspring. There are many biological causes of infertility, including some that medical intervention can treat (Makar R S, Toth T L (2002). "The evaluation of infertility". Am J Clin Pathol. 117 (Suppl): S95-103). Infertility has increased by 4 percent since the 1980s, mostly from problems with fecundity due to an increase in age (Maheshwari, A. (2008). *Human Reproduction.* pp. 538-542). About 40 percent of the issues involved with infertility are due to the man, another 40 percent due to the woman, and 20 percent result from complications with both partners (Hudson, B. (1987). *The infertile couple.* Churchill-Livingstone, Edinburgh).

In humans, environmental factors such as chemicals and the addiction to certain substances such as tobacco and alcohol have a negative impact on sperm quality decreasing the abovementioned parameters and the fecundation rate. Also, the quality of the sperm is important during insemination, both in humans and animals. There are a number of industries that depend on the quality of the sperm to increase their production. In these industries, insemination is the most widely extended method because it enables to select those genetic backgrounds more convenient to the business activity (e.g. cows with more muscle in the meat industry or producing more milk for the milk industry, faster horses for horse races, etc). Until now, despite all methods developed to conserve sperm in the time between ejaculation and insemination, there is a reduction in those parameters related to sperm quality and the success rate of the insemination during this time.

Two of the main parameters influencing male fertility in mammals are sperm (spermatozoa) motility and progressivity. Sperm motility and progressively can be impaired, for example, by certain types of medication (such as medicaments used in chemotherapy), intensive training (e.g. professional sportsmen such as cyclists) and/or environmental factors. Reductions in the motility and progressivity of spermatozoids have been shown to be the direct cause of male infertility in different mammalian species. Semen quality in different mammals, including humans, is routinely assessed in clinical practice using three main parameters: (i) sperm motility and progressivity (percentage of motile spermatozoids that are not only mobile but in addition move in the right direction), (ii) spermatozoid concentration in the ejaculate and (iii) sperm morphology. Other parameters such as membrane integrity or sperm vitality can be additionally used (Broekhuijse, M. L., H. Feitsma, and B. M. Gadella, Artificial insemination in pigs: predicting male fertility. Vet Q, 2012. 32(3-4): p. 151-7 and Franken, D. R. and S. Oehninger, Semen analysis and sperm function testing. Asian J Androl, 2012. 14(1): p. 6-13). According to Broekhuijse et al. and Franken and Oehninger, loc. lit. altered values in sperm motility and progressivity have the highest direct correlation with infertility (more than 10% depending on the measurement methods used).

Hence it is the object of the present invention to identity a compound that is useful to treat male infertility or to increase male fertility, in particular by increasing sperm motility and progressivity. As discussed, the identification of such compounds is important since they can be used to increase the fecundation rate in mammals, including humans and the productivity in those animal industries depending on semen quality.

The present invention therefore relates in a first aspect to glycolic acid or a pharmaceutically acceptable salt or ester thereof for use in the treatment or prevention of male infertility.

Also described herein is a corresponding method of treatment or prevention of a male infertility, said method comprising the administration of an therapeutically effective amount of glycolic acid or a pharmaceutically acceptable salt or ester thereof to a subject in need thereof.

Glycolic acid (GA) has the IUPAC name 2-hydroxyethanoic acid and the molecular formula $C_2H_4O_3$. Glycolic acid is used in the prior art, for example, in the textile industry as a dyeing and tanning agent, in food processing as a flavouring agent and as a preservative, and in the pharmaceutical industry as a skin care agent, in particular as a skin peeling agent. Glycolic acid can also be found in sugar beets, sugarcane and various fruits. Traces of glycolic acid are present, for example, in unripe or green grapes. Glycolic acid is also found in pineapple and cantaloupe.

The present invention employs glycolic acid or a pharmaceutically acceptable salt or ester thereof. Accordingly, the present invention may employ any one of glycolic acid, a pharmaceutically acceptable salt of glycolic acid and an ester of glycolic acid.

A pharmaceutically acceptable salt of glycolic acid includes but is not limited to potassium gylcolate, sodium gylcolate, calcium gylcolate, magnesium gylcolate, barium glycolate, aluminium gylcolate, oxalate, nitrate, sulphate, phosphate, fumarate, succinate, maleate, besylate, tosylate, tartrate, and palmitate.

A pharmaceutically acceptable ester of glycolic acid includes but is not limited to methyl glycolate, and ethyl glycolate.

The term "treatment" as used herein comprises a (partially or fully) curative treatment and in particular encompasses the stop or the deferral of the progression of the disease to be treated.

The term "prevention" as used herein is stopping or delaying the onset of the disease to be treated. The use of glycolic acid or a pharmaceutically acceptable salt or ester thereof according to the first aspect of the invention also prevents the natural decay in sperm mobility after ejaculation. In other words, glycolic acid or a pharmaceutically acceptable salt or ester thereof is capable to maintain sperm motility after ejaculation for a longer time.

The term "infertility" designates the inability of an animal to conceive sexual offspring. The term "male infertility" refers to a male's inability to cause pregnancy in a fertile female. As discussed herein above in detail, male infertility is commonly due to deficiencies in the semen (spermatozoa), and the assessment of semen quality is used in the art as a surrogate to measure of male fertility. The male infertility is in accordance with the invention the male infertility of a mammal.

The term "spermatozoon" (or sperm (cell) or semen (cell)) as used herein is a mature male germ cell, which fertilizes the oocyte in sexual reproduction and contains the genetic information for the zygote from the male. Spermatozoa are formed in male mammals in the seminiferous tubules, derived from spermatogonia, which first develop into spermatocytes; these in turn produce spermatids by meiosis, which then differentiate into spermatozoa. A spermatozoon is microscopic in size. It looks like a translucent tadpole, and has a flat, elliptical head containing a spherical centre section, and a long tail by which it propels itself with a vigorous lashing movement. Since the male infertility is in accordance with the invention the male infertility of a mammal also the spermatozoa are in accordance with the invention from a mammal.

Semen deficiencies which cause male infertility may be labelled as follows: (i) Oligospermia or oligozoospermia—decreased number of spermatozoa in semen; (ii) aspermia—complete lack of semen; (iii) hypospermia—reduced seminal volume; (iv) azoospermia—absence of sperm cells in semen; (v) teratospermia—increase in sperm with abnormal morphology, and (vi) asthenozoospermia—reduced sperm motility/mobility.

There are various combinations of these deficiencies as well, e.g. Teratoasthenozoospermia, which is reduced sperm morphology and motility. Moreover, low sperm counts are often associated with decreased sperm motility and increased abnormal morphology, thus the terms "oligoasthenoteratozoospermia" or "oligospermia" can be used as a catch all these deficiencies.

In accordance with the present invention the glycolic acid or a pharmaceutically acceptable salt or ester thereof may be comprised in a formulation. A formulation prepared in accordance with the invention comprises at least two components in an appropriate relationship two each other, wherein at least one of the two components is glycolic acid or a pharmaceutically acceptable salt or ester thereof. The second of the at least two components of a formula may be a simple carrier, for example water. A formulation may be a mixture or a structure such as a liquid, a capsule, a powder, an aerosol, a pill, a tablet, or an emulsion, prepared according to a specific procedure (called a "formula"). Formulations are a very important aspect of creating drugs. Formulas may ensure, for example, that the active ingredient of a drug—being in the present invention glycolic acid or a pharmaceutically acceptable salt or ester thereof—is delivered to the correct part of the body, in the right concentration, and/or at the right release rate (not too fast and not too slowly).

The formulation of the present invention is therefore preferably a pharmaceutical formulation. In accordance with the present invention, the term "pharmaceutical formulation" relates to a formulation for administration to a mammal, preferably a human. The pharmaceutical formulation of the invention may, optionally, comprise further molecules, for example compounds being capable of altering the characteristics of the compounds of the invention thereby, for example, stabilizing, modulating and/or activating their function. The pharmaceutical formulation of the present invention may, optionally and additionally, comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, organic solvents including DMSO etc. Formulations comprising such carriers can be formulated by well known conventional methods. These pharmaceutical formulations can be administered to the subject at a suitable dose. The dosage regimen will be determined by the attending physician and clinical factors. As is well known in the medical arts, dosages for any one mammal depend upon many factors, including the mammal's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician.

Glycolic acid (GA) is naturally present in a variety of fruits, vegetables, meats and beverages, however in amount being lower as 50 mg/kg (see Harris and Richardson (1980), Investigative Urology, 18:106-109). 50 mg/kg correspond to 0.005% (w/w). Hence, the formulation of the invention preferably comprises a higher amount/concentration of glycolic acid or a corresponding pharmaceutically acceptable salt or ester thereof than the amount of glycolic acid found in natural food.

The skilled person can determine a suitable daily dose of such formulations as well as a suitable daily dosage in case glycolic acid or a pharmaceutically acceptable salt or ester thereof are directly administered to a subject. The administered amounts of glycolic acid or a pharmaceutically acceptable salt or ester thereof on the one hand have to be sufficient for the treatment or prevention of male infertility, and on the other hand should not be so high as to generate an acidosis in the subject to be treated. Acidosis is an increased acidity in the blood and other body tissue. Acidosis is said to occur when the blood, serum or body tissue pH falls below 7.35. Means and methods to determine the pH in blood, serum and body tissue are well-known. Suitable does will be discussed herein below.

The toxic effect of too much glycolic acid is known, for example, from the 1985 diethylene glycol wine scandal. The scandal involved a limited number of Austrian wineries that had illegally adulterated their wines using the toxic substance diethylene glycol (a primary ingredient in some brands of antifreeze) to make the wines appear sweeter and more full-bodied. The major cause of toxicity is not the ethylene glycol itself but its major metabolite glycolic acid. The minimum toxic dose of diethylene glycol is estimated at 0.14 mg glycolic acid per kg of body weight and the lethal dose is estimated between 1.0 and 1.63 g/kg. Hence, the preferred dose of glycolic acid and a pharmaceutically acceptable salt or ester thereof is selected such that total glycolate levels do not exceed 0.20 mg glycolate per kg of body weight, preferably do not exceed 0.14 mg glycolate per kg of body weight, and more preferably do not exceed 0.10 mg. Preferred lower amounts to be combined with the maximum amount are with increasing preference 0.01, 0.03, 0.05, 0.075 and 0.1 mg glycolate per kg of body weight.

The therapeutic route used for the treatment or prevention of male infertility is not particularly limited. Hence, administration may be topical (local), enteral (system-wide effect, but delivered through the gastrointestinal tract), or parenteral (systemic action, but delivered by routes other than the GI tract). As regards system-wide applications the oral or intravenous route are preferred. It is though preferred that the glycolic acid or a pharmaceutically acceptable salt or ester thereof is applied directly where its action is desired and hence is administered topically, more preferably such that it is directly contacted with spermatozoa. It is to be understood that the above discussed glycolate amounts per kg of body weight has to be taken into account in particular if glycolic acid or a pharmaceutically acceptable salt or ester thereof are enterally or parenterally administered. Preferred concentrations and amounts of glycolic acid or a pharmaceutically acceptable salt or ester thereof to be present locally in the sperm probe will be further discussed herein below. Also means for directly contacting glycolic acid or a pharmaceutically acceptable salt or ester thereof with spermatozoa are provided herein below.

In the examples described herein below the effect of glycolic acid on mouse and bull sperm motility and progressivity at different time points after its administration was tested. The experimental results show that glycolic acid significantly enhances sperm motility and progressivity shortly after administration in comparison to control non-treated sperm. To the best knowledge of the inventors no study has previously tried testing the effect of glycolic acid on sperm motility and progressivity and it could not be foreseen that glycolic acid increases sperm motility and progressivity.

In accordance with a preferred embodiment of the invention, the male infertility is associated with asthenozoospermia.

Asthenozoospermia (or asthenospermia) is the medical term for reduced sperm motility or reduced sperm mobility. Sperm motility/mobility, in turn, refers to how well sperm moves. The specific ability of sperm to move ahead to reach the egg is called forward progression or progressivity. In general, sperm mobility is assessed by its progressive (i.e. directed) mobility and its overall (i.e. non-directed) motility.

The two aspects analyzed in order to diagnose a lack of sperm motility are in general: the percentage of sperm cells moving within the semen sample, and a count of the total number of moving sperm. Sperm progressivity is determined by the ability of the sperm to swim forward, thus allowing the sperm to follow a concentration gradient of signalling molecules in the vagina and uterus that guide the sperm to reach the egg in order for fertilization to happen. Progressive motility means the sperm is active, whether moving linearly. In non-progressive motility, the sperm is active although there is no forward progression. When sperm does not move, this is referred to as immotility/immobility.

When sperm has low motility or is immotile, this negatively affects male fertility. Complete asthenozoospermia, that is, 100% immotile spermatozoa in the ejaculate, is reported at a frequency of 1 of 5000 men (Ortega, C.; Verheyen, G.; Raick, D.; Camus, M.; Devroey, P.; Tournaye, H. (2011). "Absolute asthenozoospermia and ICSI: What are the options?". Human Reproduction Update 17 (5): 684-692).

In accordance with a further preferred embodiment of the invention, the glycolic acid or a pharmaceutically acceptable salt or ester thereof is to be applied inside the vagina and/or the cervix prior to or during sexual intercourse.

In order to treat or prevent male infertility the glycolic acid or a pharmaceutically acceptable salt or ester thereof is preferably directly contacted with the spermatozoa during sexual intercourse. This may be done by applying glycolic acid or a pharmaceutically acceptable salt or ester thereof to a female in accordance with the above preferred embodiment of the invention. In accordance with the above preferred embodiment the glycolic acid or a pharmaceutically acceptable salt or ester thereof is preferably comprised in the sexual lubricant composition or the virginal ring of the invention, which both will be further detailed herein below.

In accordance with another preferred embodiment of the invention, the male infertility is human male infertility.

Infertility in humans can be defined clinically in men who cannot achieve pregnancy after 1 year of having unprotected intercourse (see http://www.nichd.nih.gov/health/topics/infertility/Pages/default.aspx). As discussed herein above, many different medical conditions and other factors can contribute to fertility problems. Currently many scientists are conducting research to identify both the causes of infertility and new treatments that may allow more men and women to achieve pregnancy. Hence, applying the means and methods of the invention to human sperm is particularly preferred.

In accordance with still another preferred embodiment of the invention, the male infertility is male infertility of a mammalian production animal, mammalian domestic animal, zoo mammal or endangered mammal.

In addition to male infertility in humans also the treatment of male infertility in mammalian production animals or mammalian domestic animal is of great commercial interest. Non-limiting examples of a production animals or mammalian domestic animal are cat, dog, cattle, horse, donkey, mouse, rat, rabbit, pig, sheep, goat and Guinea pig. Non-limiting examples of a zoo mammal or a endangered mammal are elephants, tigers, leopard, lion, ape (e.g. gorilla or chimpanzee), monkey (e.g. lion tamarin), giraffe, rhino, polar bear, buffalo, dolphin and whale.

The present invention relates in a second aspect but related aspect to an ex vivo method for increasing the mobility of spermatozoa comprising contacting glycolic acid or a pharmaceutically acceptable salt or ester thereof with spermatozoa.

In a non-harmful environment outside the body, such as in a sterile glass container the number of motile sperm in humans decreases with approximately 5-10% per hour (Gerris J (1999). "Methods of semen collection not based on masturbation or surgical sperm retrieval". Human Reproduction Update 5 (3): 211-5). The method of the invention is therefore particularly useful for the treatment of spermatozoa before they are used for artificial insemination process, such as in vitro fertilization processes in humans or other mammals.

Artificial insemination is the deliberate introduction of semen (spermatozoa) into a female's vagina or oviduct for the purpose of achieving a pregnancy through fertilization by means other than sexual intercourse. In vitro fertilisation is a process by which an egg is fertilised by sperm outside the body. Artificial insemination is the medical alternative to sexual intercourse. Artificial insemination is a common fertility treatment for humans as well as a common practice in the breeding of animals, for example dairy cattle. Hence, also in accordance this method the spermatozoa are preferably from human, a mammalian production animal, mammalian domestic animal, zoo mammal or endangered mammal.

In accordance with a preferred embodiment of the method of the invention, the spermatozoa are defrosted spermatozoa.

In particular for breeding of animals and for humans sperm banks exist. A sperm bank (or semen bank or cryobank) is a facility that collects and stores human sperm or animal sperm in frozen form for a later use in achieving pregnancy in a female. Sperm banks may 'wash' the sperm sample to extract sperm from the rest of the material in the semen. A cryoprotectant semen extender is usually added before the sperm is to be placed in frozen storage. Before the cryopreserved sperm is used for artificial insemination it is defrosted. Such defrosted spermatozoa are used for the method of the invention in accordance with the above preferred embodiment of the method of the invention.

In accordance with a further preferred embodiment of the method of the invention, the spermatozoa are human spermatozoa.

The first successful birth of a "test tube baby" after in vitro fertilisation (IVF), Louise Brown, occurred in 1978. Louise Brown was born as a result of natural cycle IVF where no stimulation was made. Since then in vitro fertilisation became standard method for aiding human couples with infertility problems and Robert G. Edwards, the physiologist who developed the treatment, was awarded the Nobel Prize in Physiology or Medicine in 2010.

The present invention relates in a third and related aspect to a composition comprising glycolic acid or a pharmaceutically acceptable salt or ester thereof, and a further compound increasing male fertility.

The further compound may be useful to treat or prevent one or more of semen deficiencies which cause male infertility, namely (i) oligospermia or oligozoospermia; (ii) aspermia; (iii) hypospermia; (iv) azoospermia; (v) teratospermia, and (vi) asthenozoospermia. The composition is particularly useful if combinations of these semen deficiencies occur in a subject, e.g. Teratoasthenozoospermia, or oligoasthenoteratozoospermia.

For example, several drugs are available to treat pituitary and hormonal imbalances which can cause male infertility. If luteinizing hormone (LH) and follicle-stimulating hormone (FSH) levels are low and the hypothalamus and pituitary gland are functional, the drug clomiphene citrate (Serophene, Clomid) is able to stimulate the hypothalamus to release gonadotropin-releasing hormone (GnRH) at regular intervals and restore fertility. If the pituitary is malfunctioning and not manufacturing the necessary sex hormones, hormone replacement therapy can restore fertility. Injections of hCG (human chorionic gonadotropin) increases the LH supply and can stimulate the testes to produce testosterone and sperm. If unresponsive to hCG, the drug Pergonal (a combination of LH and FSH) can stimulate sperm production. The drug Parlodel (bromocriptine) can correct hyperprolactinemia. Cortisone replacement therapy can lower abnormally high androgen levels and allow the pituitary to function normally to restore fertility. Hormone replacement therapy usually works in about 4 months.

US patent application 20070060620 describes RAR retinoid selective compounds as a tool to facilitate sperm motility. US 20040171144 describes TNFalpha, IL1beta, IL6 inhibitors as tools to facilitate sperm motility and CN 103352025 describes a medium containing fructose 6-phosphoric acid as a tool to facilitate sperm motility in vitro. All these examples may be used as a further compound increasing male fertility.

Moreover, ashwagandha, astaxanthin, *Eurycoma longifolia,* maca, progesterone, saffron or *Vitex agnus*-castus may be used as a further compound increasing male fertility. All these compounds are known in the art for the treatment or prevention of male infertility, in particular Asthenozoospermia. Ashwagandha is a plant. The root and berry are used to produce medicines. Astaxanthin is a reddish pigment that belongs to a group of chemicals called carotenoids. It occurs naturally in certain algae and causes the pink or red color in salmon, trout, lobster, shrimp, and other seafood. *Eurycoma longifolia* is a tall, slender evergreen shrub-tree commonly found in Southeast Asia. Malaysian men claim that tea made from this plant improves their sexual abilities and virility. Maca is a plant that grows in central Peru in the high plateaus of the Andes mountains. Its root is used to produce medicines. Progesterone is an endogenous steroid hormone involved in the menstrual cycle, pregnancy, and embryogenesis of humans and other species. Saffron is a spice derived from the flower of *Crocus sativus,* commonly known as the saffron crocus. The stigmas of *Crocus sativus* are used to produce medicines. *Vitex agnus*-castus is the fruit of the chaste tree. The fruit and seed are used to produce medicine.

In accordance with a preferred embodiment of the method of the invention, the further compound is/are (i) an antioxidants, preferably coenzyme Q10, (ii) a vitamin, preferably selected from one or more of Vitamin D, E, C, B2, B9, and/or (iii) one or more of L-arginine, L-carnitine and L-creatine.

Lafuente Ret al., Reprod Genet. 2013 September; 30(9): 1147-56 report that among male patients receiving CoQ10 treatment, a statistically significant increase in sperm concentration and sperm motility occured. Similar observations have been made by Mancini A, Balercia G. Biofactors. 2011 September-October; 37(5):374-80.

In men, the vitamin status has been associated with semen quality and sperm count, motility and morphology (Walczak-Jedrzejowska R, Wolski J K, Slowikowska-Hilczer J. Cent European J Urol. 2013; 66(1):60-7, and Anagnostis P, Karras S, Goulis D G, Int J Clin Pract. 2013 March; 67(3):225-35).

The effect of L-arginine to enhance motility and metabolic rate in spermatozoa is reported in Srivastava S, Agarwal A. Andrologia. 2010 April; 42(2):76-82. Furthermore, L-carnitine is known to improve sperm mobility (see Manee-In S, Parmornsupornvichit S, Kraiprayoon S, Tharasanit T, Chanapiwat P, Kaeoket K. Asian-Australas J Anim Sci. 2014 June; 27(6):791-6). Finally, L-creatine may enhance sperm mobility.

The present invention relates in a fourth and related aspect to the use of glycolic acid or a pharmaceutically acceptable salt or ester thereof for the preparation of a sexual lubricating composition which promotes male fertility.

The sexual lubricating composition can be applied to the vagina including the cervix, the penis, or both. As discussed herein above the glycolic acid or a pharmaceutically acceptable salt or ester thereof is preferably to be applied inside the vagina and/or the cervix prior to or during sexual intercourse. In particular for this application the glycolic acid or a pharmaceutically acceptable salt or ester thereof may be comprised in a sexual lubricating composition. Ingredients of sexual lubricating compositions are well known in the art. For instance, the sexual lubricating composition may be water-based, oil-based or silicone-based. Water-based lubricants are the most widely used personal lubricants. The earliest water-based lubricants were cellulose ether or glycerin solutions. Oil-based lubricants may comprise baby oil, olive oil, canola oil, or mineral oil. Silicone-based lubricants are usually formulated with fewer than four ingredients and do not contain any water. Certain commonly used commercial lubricants have been found to impair sperm function. It is to be understood that such lubricants are not used in accordance with the invention. The chemical properties of the lubricant, such as osmolarity or pH are to be selected such that sperm function is not impaired.

In accordance with a preferred embodiment of the use of the invention, the sexual lubricating composition is a sexual lubricating cream or a sexual lubricating oil.

Lubricants such as mineral oil, canola oil, or hydroxyethylcellulose-based lubricants are recommended for use by couples attempting conception and accordingly particularly preferred in accordance with the invention. Oils may also be used to obtain a cream.

The present invention relates in a fifth and related aspect to a vaginal ring which releases glycolic acid or a pharmaceutically acceptable salt or ester thereof when placed in the vagina.

As discussed herein above, the glycolic acid or a pharmaceutically acceptable salt or ester thereof is preferably to be applied inside the vagina and/or the cervix prior to or during sexual intercourse. In particular for this application the glycolic acid or a pharmaceutically acceptable salt or ester thereof may be comprised with a vaginal ring to be inserted into the vagina.

Vaginal rings (also known as intravaginal rings, or V-Rings) are known in the art and are usually polymeric drug delivery devices designed to provide controlled release of drugs for intravaginal administration over extended periods of time. The vaginal ring of the invention provides glycolic acid or a pharmaceutically acceptable salt or ester thereof and may additionally provide one or more of the further compounds increasing male fertility discussed herein above. Vaginal rings are easily inserted and removed. Vaginal walls hold them in place. Although their exact location within the vagina is not critical for clinical efficacy, rings commonly reside next to the cervix. Rings are typically left in place during intercourse.

In accordance with a preferred embodiment of all five aspects of the invention, the glycolic acid or a pharmaceutically acceptable salt or ester thereof is used/comprised at least at a concentration of 5 mM, preferably 10 mM, more preferably 20 mM and most preferably 30 mM.

In accordance with this preferred embodiment and preferred examples thereof the indicated concentration of glycolic acid or a pharmaceutically acceptable salt or ester thereof designates the final concentration of glycolic acid or a pharmaceutically acceptable salt or ester thereof in the sperm sample to be used/treated.

As it is evident from the examples and figures herein below the concentration of glycolic acid used for the experiments with mouse and bull sperm was 10 to 30 mM. Moreover, as glycolic acid at 10 mM increased sperm mobility, in particular sperm progressivity in mouse and bull sperm it can be assumed that this concentration or higher also increases sperm mobility and sperm progressivity in other mammalian species, in particular humans. Also lower concentrations of glycolic acid or a pharmaceutically acceptable salt or ester thereof of at least 5 mM or of at least 7.5 mM are believed to increase sperm mobility, in particular sperm progressivity.

The Applicant has also applied glycolic acid at concentrations up to 60 mM to bull sperm (data not shown). Also at this higher concentrations an increase of sperm mobility, in particular sperm progressivity was observed. The most efficient concentration in mice is between 10 mM and 20 mM and in bulls between and 30 mM to 60 mM. It is believed that the difference of the optimal concentration between mouse and bull is due to the different sperm count in normal sperm concentrations in the ejaculate. For instance, 15 million sperm per milliliter is considered normal in humans while concentration ranges between 300-2500 million/ml (1200 millions/ml is the mean value) is considered normal in bulls. For mice a normal sperm count of around 75 million sperm per ml was reported (Schürmann et al. (2002), Mol Cell Biol. April 2002; 22(8): 2761-2768.). Hence, it is to be understood that above a concentration of at least 10 mM, which is believed to work in all mammalian species, the ideal concentration may slightly vary between different species or even within one species between different races (e.g. dog races).

With respect to the above preferred embodiment of all five aspects of the invention it is preferred that the glycolic acid or a pharmaceutically acceptable salt or ester thereof is used/comprised at the most at a concentration of 250 mM, preferably 125 mM, more preferably 100 mM and most preferably 70 mM. As regards preferred ranges, the various indicated individual minimum and maximum concentration may be freely combined. Hence, contemplated are by the present invention, inter alia and with increasing preference concentration ranges of 5 mM to 250 mM, 7.5 mM to 125 mM and, 10 mM to 100 mM, and 10 mM to 70 mM.

In accordance with a further preferred embodiment of all five aspects of the invention, the glycolic acid or a pharmaceutically acceptable salt or ester thereof is used/comprised at least in amounts of about 380.25 µg/1200 million spermatozoa, preferably about 760.5 µg/1200 million spermatozoa, more preferably about 1521 µg/1200 million spermatozoa, and most preferably about 2281.5 µg/1200 million spermatozoa.

In accordance with this preferred embodiment the indicated concentration of glycolic acid or a pharmaceutically acceptable salt or ester thereof designates the amount of glycolic acid or a pharmaceutically acceptable salt or ester thereof in the sperm sample to be used/treated based on the mean value of 1200 million spermatozoa/ml of bull sperm. The indicated amounts of glycolic acid or a pharmaceutically acceptable salt or ester thereof are particularly useful in case the sperm sample is a sperm sample comprising the normal (i.e. wild-type) number of sperms in bull. Such a sperm sample may be fresh bull ejaculate or a defrosted bull sperm sample, wherein the sperm count has not been substantially changed. Based on the exemplified amounts of glycolic acid or a pharmaceutically acceptable salt or ester thereof for normal bull sperm the skilled person can calculate the amounts of glycolic acid or a pharmaceutically acceptable salt or ester for other mammals based on the mean value of spermatozoa/ml in the respective mammal. Also in case a mammal is afflicted with oligospermia or oligozoospermia the skilled person can adapt the amounts of glycolic acid or a pharmaceutically acceptable salt or ester thereof to the decreased number of spermatozoa. The skilled person can likewise adapt the amounts of glycolic acid or a pharmaceutically acceptable salt or ester thereof to an increased number of spermatozoa, for example in case a concentrated sperm sample is to be used/treated.

With respect to the above preferred embodiment of all five aspects of the invention it is preferred that the glycolic acid or a pharmaceutically acceptable salt or ester thereof is used/comprised at the most in amounts of about 19012.5 µg/1200 million spermatozoa, preferably about 9506.25 µg/1200 million spermatozoa, more preferably about 7605 µg/1200 million spermatozoa, and most preferably about 5323.5 µg/1200 million spermatozoa. As regards preferred amount, the various indicated individual minimum and maximum amount may be freely combined. Hence, contemplated are by the present invention, inter alia and with increasing preference amounts in the ranges of about 380.25 to about 19125 µg/1200 million spermatozoa, about 570.375 to about 9562.5 µg/1200 million spermatozoa, about 760.5 to about 7605 µg/1200 million spermatozoa, and about 760.5 to about 5323.5 µg/1200 million spermatozoa. In this connection the term "about" means preferably ±25 µg.

The figures show:

FIG. 1: Mouse sperm motility after 30 min. 10 mM glycolic acid.

Figure 2:
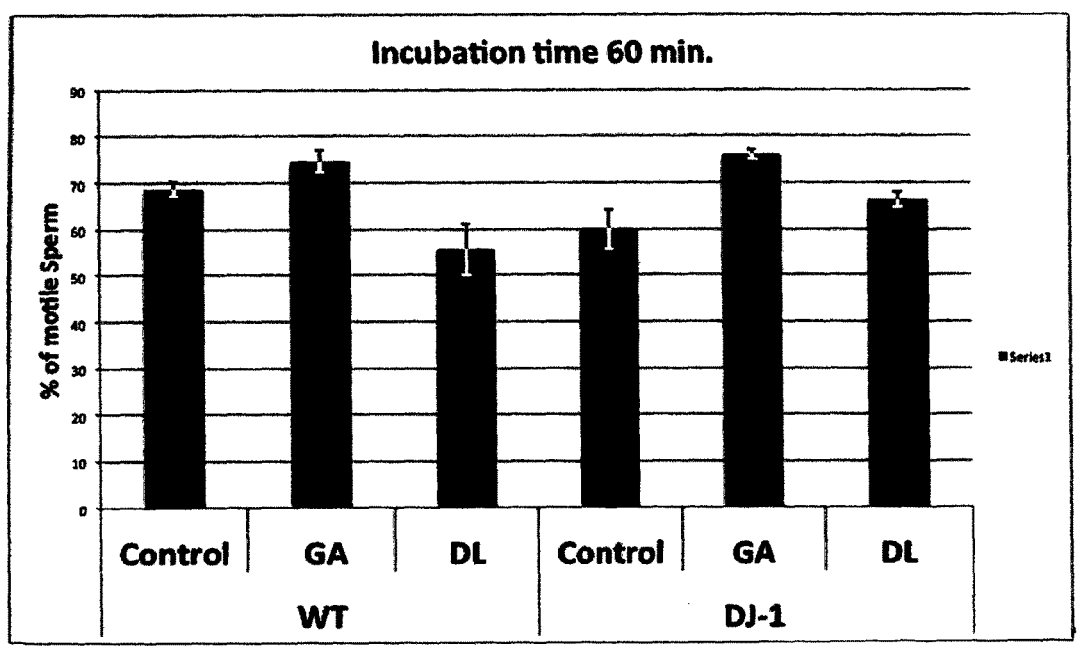

FIG. 2: Mouse sperm motility after 60 min. 10 mM glycolic acid

Figure 3:
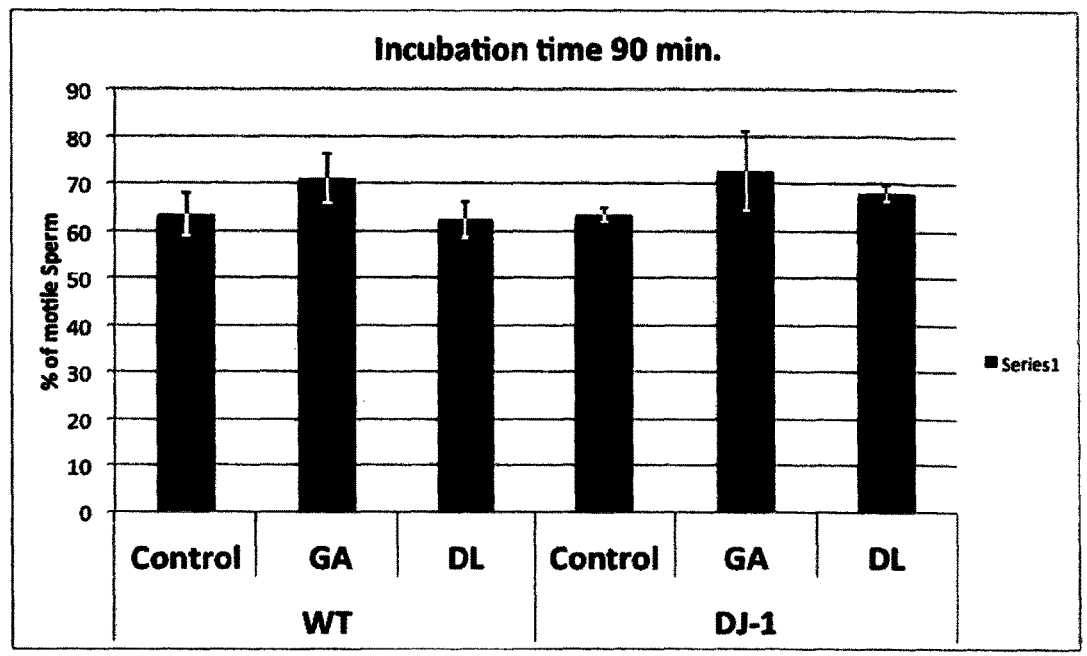

FIG. 3: Mouse sperm motility after 90 min. 10 mM glycolic acid.

Figure 4:
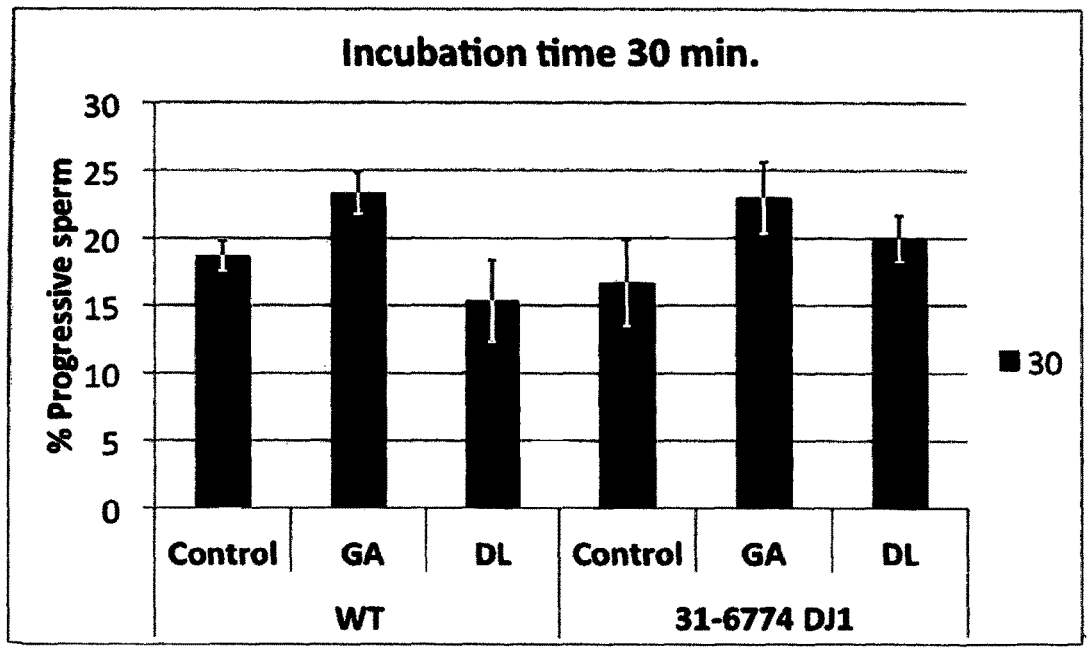

FIG. 4: Mouse sperm progressivity after 30 minutes. 10 mM glycolic acid.

Figure 5:
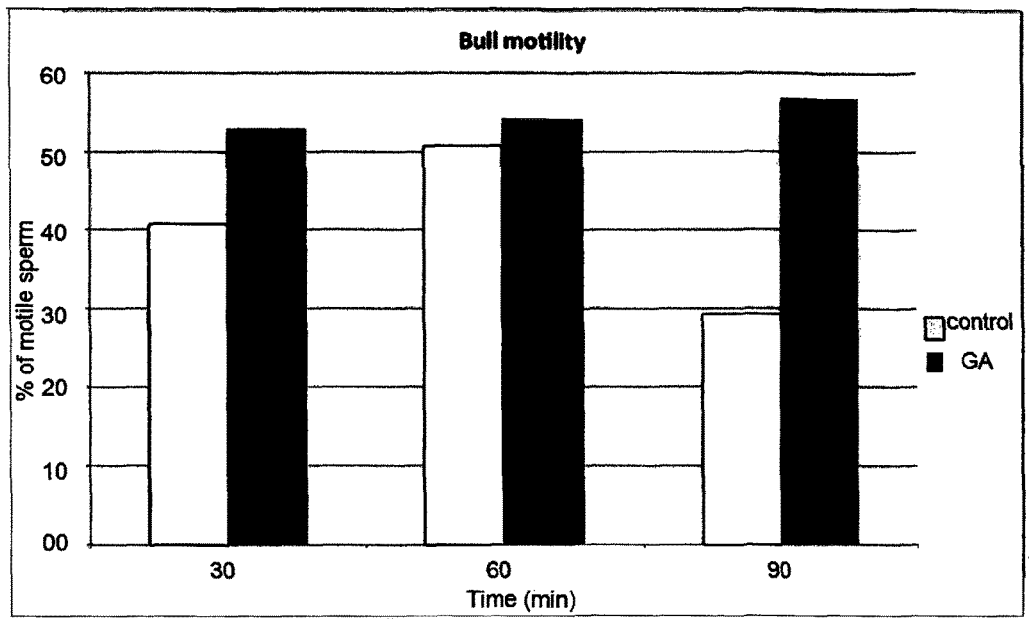

FIG. 5: Sperm motility in bulls. 10 mM glycolic acid.

Figure 6:
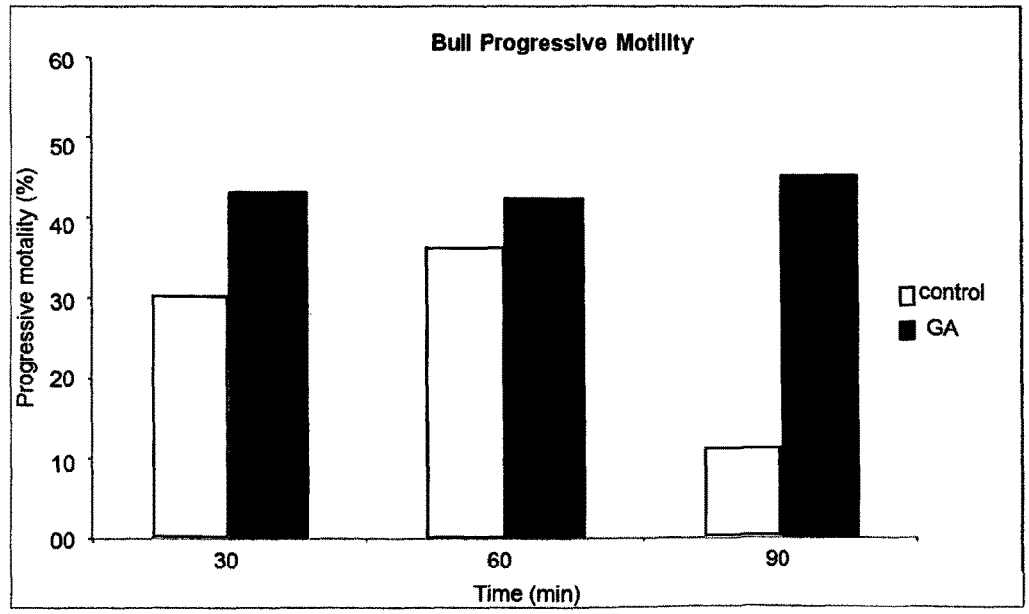

FIG. 6: Sperm progressivity in bulls. 10 mM glycolic acid.

Figure 7:
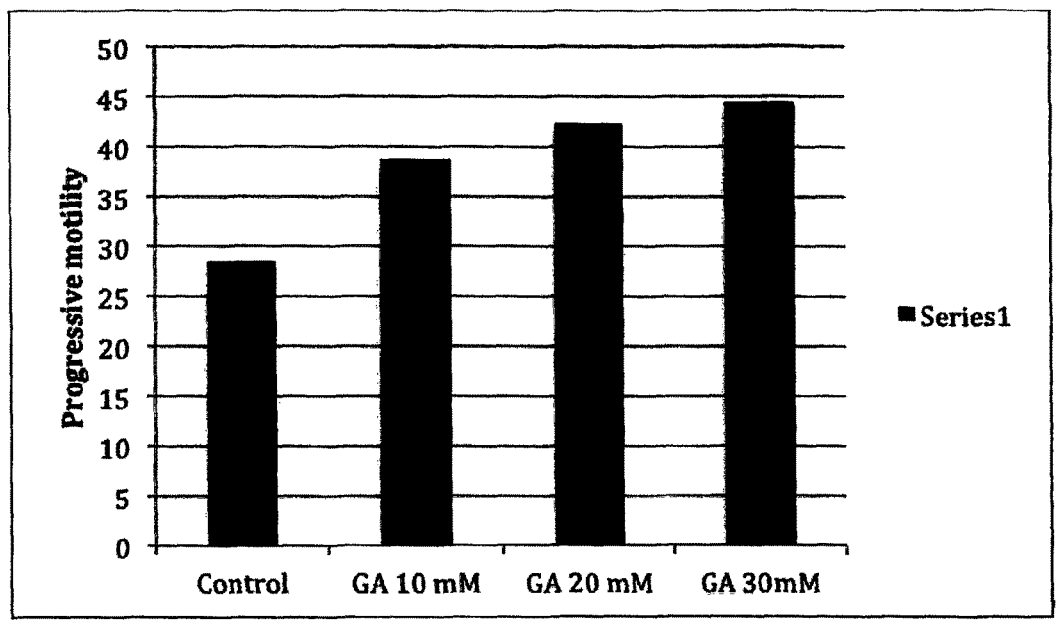

FIG. 7: Comparison of sperm progressive motility in bulls after 90 min. between treatment with 10, 20 and 30 mM glycolic acid.

FIG. 8: Glycolic acid enhances sperm motility in human and bull sperm.

The examples illustrate the invention.

EXAMPLE 1

Material and Methods

Mouse:

Extract epididymis and open them in CPA medium (18% Raffinose and 3% Low fat milk powder). Let spermatozoids swim out for 5 min at room temperature.

For each condition, take 4 μl of mouse sperm in CPA and place in 196 μl of HTF medium from the incubator (at 37° C.). Let it incubate 5 min. in the 37° C. incubator, add substances to the HTF medium (see formulation below) and incubate for different times.

At each time point, fill a Leja-Slide with 25 μl of the HTF buffer containing the diluted sperm and place in the sperm counting machine (Hamilton-Thorne, USA). The machine takes 10 pictures per samples and analyses the different parameters (motility, progressivity,etc. . . . ). Sperm motility analysis was done blindly. Glycolic acid and D-lactate were given to the technician from the facility as Substance 1 and Substance 2, only later did she get to know which belong to what compound.

Bull:

Frozen bull sperm was defrosted in a warm bath and centrifuged. The supernatant was removed and the sperms were resuspended in HTF-like medium alone or with glycolic acid. Sperms were incubated with the 10, 20 and 30 mM glycolic acid for 10 min. before the measurements began. Measurements were performed by an experienced technician from the urology department.

Human:

Human sperm was collected from donors after ejaculation and used on the same day. Frozen human sperm was defrosted in a warm bath before starting the experiments. The regional ethical committee approved sample collection and use of human sperm. Both fresh and frozen human sperm were centrifuged, the supernatant was removed and the sperms were resuspended in HTF-like medium alone or with glycolic acid. Sperms were incubated with the 30 and 60 mM glycolic acid for 10 min before the measurements began. Measurements were performed by an experienced technician from the urology department.

EXAMPLE 2

Experimental Outline

The examples tested the effect of 10 to 30 mM of glycolic acid and D-lactate on mouse sperm motility and progressivity or on bull motility. For this, epididymic mouse sperm from two strains (WT and DJ-1) or ejaculated frozen bull sperm was obtained. Sperm from each individual was divided and treated either with glycolic acid or with the vehicle for up to 90 minutes. Mouse sperm motility and progressivity was determined with the help of an automatized machine (CASA system, Hamilton-Thorne Research, http://www.hamiltonthorne.com/index.php/products/casa-products/sperm-analysis-systems-research) that uses high frequency photo images and image analysis to analyze these parameters. Frozen ejaculated bull sperm motility was assessed by an experienced technician. Mouse sperm from WT and DJ-1 mice was divided by the software into motile and non-motile sperm according to standardized parameters and results are given as percentages of the total population identified as motile sperm (FIG. 1-4). Sperm progressivity alone was analyzed only on the mouse sperm, as only the software from the CASA system is sensitive enough to make this analysis and this machine can only analyze mouse sperm. Bull sperm was divided into progressive motile, motile (the sum of progressive motile and motile on the spot) and the rest (FIGS. 5, 6 and 7).

EXAMPLE 3

Experimental Results

The results depicted in FIGS. 1 to 5 show that mouse and bull sperm motility and progressivity are significantly enhanced upon appliance of glycolic acid.

Addition of 10 mM of Glycolic acid to ejaculated sperm increases sperm motility (percentage of motile spermatozoids) and sperm progressivity (percentage of motile spermatozoids that move forward or progressive) by an average of 19% (motility) and 28% (progressivity) respectively 30 minutes after the application in mouse and bull sperm (FIGS. 1-6). Similar results were obtained after 60 and 90 minutes (FIG. 1-6). A further increase in bull sperm motility and progressivity values when compared to 10 mM glycolic acid was obtained when using higher concentrations (20 and 30 mM) of glycolic acid. Sperm motility and sperm progressivity are key indicators of sperm quality and are strongly associated with fecundation rates and male fertility. Thus, improving sperm motility and progressivity is expected to have a direct effect on the fecundation rate. This can be observed both in WT and DJ-1 mice.

This enhancement has been consistently observed over all experiments and may vary with dosage, time and between species in a range from 10 to 40% when compared to controls. Importantly, this increase in motility is almost all due to an increase in the proportion of progressive motile spermatozoids. Thus, suggesting that, in these concentrations, glycolic acid has a strong effect on the quality of the movement. Interestingly, in mouse sperm a significance difference in the sperm treated with GA has been observed but not with D-lactate when compared to the controls. The enhancement is sustained over time up to 90 min in both species.

EXAMPLE 4

Results on Sperm Motility and Mitochondrial Activity Upon Application of Glycolic Acid FIG. 8 shows that glycolic acid enhances sperm motility in human and bull sperm. This enhancement can be observed in human sperm, both defrosted and fresh, and defrosted bull sperm. Two-way ANOVA analysis was used (much more restrictive than a t-Test). * means $p<0.05$, $p<0.01$, *$p<0.001$ and ***$p<0.0001$. On top of the differences for each time point between the different treatment groups, if all time-points were taken together and analyzed as a whole, the results show that GA induced a significant ($p<0.05$) increase in sperm motility throughout the whole experiment when compared to the control (i.e. GA treated sperm was higher in every time point when compared to controls). Interestingly, glycolic acid did not increase the mitochondrial membrane potential, and may even decrease it (see FIG. 8). This was measured using JC-1 and FACS sorting to determine the percentage of sperms that was active and the percentage that was inactive. Both sperm motility and mitochondrial measurements are normalized to a control at time-point 0.

The invention claimed is:

1. A method of treatment of male infertility associated with impaired sperm motility or oligospermia, or for reducing decay in sperm motility after ejaculation, comprising:
   administering a composition comprising glycolic acid or a pharmaceutically acceptable salt or ester thereof effective to improve sperm motility to a subject in need thereof, thereby contacting said glycolic acid or a pharmaceutically acceptable salt or ester thereof with spermatozoa in-vivo for the treatment of the male infertility associated with impaired sperm motility or oligospermia, or for reducing decay in sperm motility after ejaculation.

2. The method of claim 1, wherein the male infertility is associated with asthenozoospermia.

3. The method of claim 1, wherein the glycolic acid or a pharmaceutically acceptable salt or ester thereof is to be applied inside the vagina and/or the cervix prior to sexual intercourse.

4. The method of claim 1, wherein the male infertility is human male infertility.

5. The method of claim 1, wherein the male infertility is male infertility of a production animal, mammalian domestic animal, zoo mammal or an endangered mammal.

6. An ex vivo method for increasing the mobility of spermatozoa comprising contacting glycolic acid or a pharmaceutically acceptable salt or ester thereof with spermatozoa in need of increasing mobility wherein the contacting step is performed ex vivo and the mobility of the spermatozoa is increased.

7. The method of claim 6, wherein the spermatozoa are defrosted spermatozoa.

8. The method of claim 6, wherein the spermatozoa are human spermatozoa.

9. The method of claim 1 wherein the glycolic acid or a pharmaceutically acceptable salt or ester thereof is at least at a concentration of 5 mM, and/or is at least in amounts of about 380.25 pg/1200 million spermatozoa.

10. The method of claim 6 wherein the glycolic acid or a pharmaceutically acceptable salt or ester thereof is at least at a concentration of 5 mM, and/or is at least in amounts of about 380.25 pg/1200 million spermatozoa.

11. The method of claim 1, wherein the glycolic acid or a pharmaceutically acceptable salt or ester thereof is applied inside the vagina and/or the cervix at a pH value such that sperm function is not impaired.

12. The method of claim 1, wherein the pharmaceutically acceptable salt of glycolic acid is selected from the group consisting of potassium glycolate, sodium glycolate, calcium glycolate, magnesium glycolate, barium glycolate, aluminum glycolate, oxalate, nitrate, sulphate, phosphate, fumarate, succinate, maleate, besylate, tosylate, tartrate, and palmitate.

* * * * *